United States Patent [19]
Zacharias et al.

[11] Patent Number: 6,010,972
[45] Date of Patent: Jan. 4, 2000

[54] OIL-RESISTANT DISPOSABLE ABSORBENT PRODUCT

[75] Inventors: Duane Kenneth Zacharias, Neenah; Ruth Ann Lachapell, Menasha; Brian Keith Nortman, Appleton, all of Wis.; Douglas Allen Woller, Riverdale, Utah

[73] Assignee: Kimberly-Clark Worldwide, Inc., Neenah, Wis.

[21] Appl. No.: 08/824,651

[22] Filed: Mar. 24, 1997

Related U.S. Application Data

[60] Provisional application No. 60/015,474, Apr. 15, 1996.

[51] Int. Cl.⁷ ................................................. B32B 27/00
[52] U.S. Cl. .................. 442/398; 428/304.4; 428/316.6; 428/317.5; 428/317.7; 442/185; 442/221; 442/239; 442/255; 442/268; 442/286; 442/290; 442/370; 442/381; 442/394; 442/398
[58] Field of Search .............................. 428/304.4, 316.6, 428/317.5, 317.7; 442/185, 221, 239, 255, 268, 286, 290, 370, 381, 394, 398

[56] References Cited

U.S. PATENT DOCUMENTS

| | | | |
|---|---|---|---|
| 4,372,460 | 2/1983 | Brochman et al. | 220/258 |
| 4,643,730 | 2/1987 | Chen et al. | 604/390 |
| 4,681,576 | 7/1987 | Colon et al. | 604/361 |
| 4,743,238 | 5/1988 | Colon et al. | 604/361 |
| 5,035,691 | 7/1991 | Zimmel et al. | 604/361 |
| 5,089,548 | 2/1992 | Zimmel et al. | 524/272 |
| 5,244,995 | 9/1993 | Skillicorn et al. | 526/340 |
| 5,356,963 | 10/1994 | Kauffman et al. | 524/43 |
| 5,536,563 | 7/1996 | Shah et al. | 428/224 |

FOREIGN PATENT DOCUMENTS

| | | | |
|---|---|---|---|
| 0 314 495 A2 | 5/1989 | European Pat. Off. | C09J 3/14 |
| 0 386 815 A2 | 9/1990 | European Pat. Off. | A61F 13/15 |
| 0 677 284 A1 | 10/1995 | European Pat. Off. | A61F 13/15 |
| WO 94/01507 A1 | 1/1994 | WIPO | C09J 109/06 |
| WO 94/10257 A1 | 5/1994 | WIPO | C09J 167/04 |
| WO 95/02647 A1 | 1/1995 | WIPO | C09J 129/00 |
| WO 95/02649 A1 | 1/1995 | WIPO | C09J 167/04 |
| WO 95/03361 A1 | 2/1995 | WIPO | C08K 5/10 |
| WO 95/18191 A1 | 7/1995 | WIPO | C09J 167/00 |

OTHER PUBLICATIONS

Derwent World Patent Database abstract of JP 58–135,622: Description of Honshu Paper Mfg. Co. Ltd., "Manufacturing Metallised Paper or Plastics Film for Capacitor." Aug. 12, 1983.

Derwent World Patent Database abstract of JP 62–263,893: Description of Toyo Rubber Ind. Co. Ltd., "Corrosion Prevention to Welded Line of Petroleum Tank." Nov. 16, 1987.

Derwent World Patent Database abstract of JP 3–033,200: Description of Suminoe Textile, "Leather–Like Laminate Having Good Wear and Light Resistance." Feb. 13, 1991.

Derwent World Patent Database abstract of JP 5–283,713: Description of Mitsubishi Electric Corp., "Semiconductor Sensor." Oct. 29, 1993.

American Society for Testing Materials (ASTM) Designation: D 1876–61 T, "Tentative Method of Test For Peel Resistance of Adhesives (T–Peel Test)," pp. 635–638, published 1961.

American Society for Testing Materials (ASTM) Designation: D 1921–89, "Standard Test Methods for Particle Size (Sieve Analysis) of Plastic Materials," pp. 493–496, published Aug. 1989.

American Society for Testing Materials (ASTM) Designation: D 3236–88, "Standard Test Method for Apparent Viscosity of Hot Melt Adhesives and Coating Materials," pp. 326–331, published Dec. 1988.

American Society for Testing Materials (ASTM) Designation: D 4440–93, "Standard Practice for Rheological Measurement of Polymer Melts Using Dynamic Mechanical Procedures," pp. 46–48, published Dec. 1993.

Allcock, Harry R. and Frederick W, Lampe, *Contemporary Polymer Chemistry*, Prentice Hall, 1990, pp. 15, 43, and 146.

Cheremisinoff, Nicholas P., Ph.D., *Elastomer Technology Handbook*, CRC Press, 1993, Chapter 24, pp. 835–856.

Ferry, John D., *Viscoelastic Properties of Polymers*, John Wiley & Sons, 1980, Third Edition, pp. 41–43.

Hiemenz. Paul C., *Principles of Colloid and Surface Chemistry*, Marcel Dekker, Inc., 1977, Chapter 2, pp. 42–83 and Chapter 5, pp. 160–208.

*Primary Examiner*—Helen L. Pezzuto
*Attorney, Agent, or Firm*—Sebastian C. Pugliese

[57] ABSTRACT

Disclosed is an adhesive that exhibits desired oil-resistance and processing properties. The adhesive is suitable for use in elastic composites and disposable absorbent products. In one embodiment, the adhesive exhibits the following properties: an Elastic Modulus value that is greater than about $4 \times 10^5$ dynes per square centimeter at 40° C. across the frequency range of about 0.1 to about 100 radians per second; an Elastic Modulus in Oil value that is greater than about $4 \times 10^5$ dynes per square centimeter at 40° C. across the frequency range of about 0.1 to about 100 radians per second; a Viscosity value of less than about 40,000 centipoise at a temperature of about 275° F.; and a Viscosity value of greater than about 60,000 centipoise at a temperature of about 250° F.

18 Claims, No Drawings

OIL-RESISTANT DISPOSABLE ABSORBENT PRODUCT

This application claims priority from U.S. Provisional Application No. 60/015,474 filed on Apr. 15, 1996.

BACKGROUND OF THE INVENTION

1. Field of the Invention

The present invention relates to adhesives suitable for use in elastic composites and disposable absorbent products that are insulted with a solvent comprising an oil. More particularly, the present invention relates to an adhesive that exhibits desired rheological and processing properties so as to provide effective oil-resistant bonds.

2. Description of the Related Art

The use of adhesive materials in disposable absorbent personal care products is generally known. Such adhesive materials are generally employed in absorbent products such as diapers, training pants, adult incontinence products, and feminine care products in order to attach various parts of the product together or to hold a particular part in a desired location.

A disposable absorbent product is generally designed to be insulted during use with various liquids such as water, saline, and body liquids such as urine, menses, and blood. Obviously, it is desired that the disposable absorbent product retains its integrity during use and does not allow leakage of such liquids insulting the product. As such, adhesive materials used in disposable absorbent personal care products are generally not substantially affected by such liquids so as not to substantially lose their adhesive properties during use by a wearer.

However, in addition to such liquids, the disposable absorbent product may also be insulted with oil-based solvents such as baby oil, lotions, ointments, petroleum jellies, sunscreens, or other skin care products. Unfortunately, current adhesive materials used in disposable absorbent products have been found to not be substantially resistant to such oil-based solvents and, as such, substantially lose their adhesive properties during use by a wearer when the disposable absorbent product is insulted with such an oil-based solvent. This typically results in various parts of the disposable absorbent product detaching from each other and/or in an increased incidence of liquid leaks.

For example, a composite comprising elastic threads sandwiched between two substrates may be used within a disposable absorbent product for improved fit and comfort to a wearer or for improved absorbent properties of the disposable absorbent product by reducing the incidence of leaks. An adhesive used to prepare such a composite must generally not only hold the elastic threads in place between the two substrates but also keep the elastic threads from delaminating from the substrates during use. If such an adhesive is not oil-resistant and the elastic composite is insulted with an oil-based solvent, the elastic threads may delaminate from the substrates, possibly resulting in increased liquid leaks as well as reduced fit and comfort to a wearer.

It is therefore desired to develop an adhesive that is generally oil-resistant and yet is easy to process so as to be efficiently used in the preparation of an elastic composite or a disposable absorbent product. Such an elastic composite or a disposable absorbent product would therefore better retain its integrity during use by a wearer when the elastic composite or disposable absorbent product is contacted with an oil-based solvent during such use.

SUMMARY OF THE INVENTION

In one aspect, the present invention concerns an adhesive that is substantially resistant to an oil-based solvent and which is easy to process.

In one embodiment of the present invention, an adhesive exhibits the following properties:

a) an Elastic Modulus value that is greater than about $4 \times 10^5$ dynes per square centimeter at 40° C. across the frequency range of about 0.1 to about 100 radians per second;

b) an Elastic Modulus in Oil value that is greater than about $4 \times 10^5$ dynes per square centimeter at 40° C. across the frequency range of about 0.1 to about 100 radians per second;

c) a Viscosity value of less than about 40,000 centipoise at a temperature of about 275° F.; and d) a Viscosity value of greater than about 60,000 centipoise at a temperature of about 250° F.

In another aspect, the present invention concerns an elastic composite comprising elastic threads located between a first substrate and a second substrate wherein the first substrate is attached to the second substrate by an adhesive that exhibits the desired properties described herein. The elastic composite is suitable for use in disposable absorbent products.

In one embodiment of the present invention, an elastic composite comprises elastic threads located between a first substrate and a second substrate wherein the first substrate is attached to the second substrate by an adhesive that exhibits the desired properties described herein.

In another aspect, it is desirable to provide a disposable absorbent product, such as an infant diaper, which product is substantially oil-resistant so that the disposable absorbent product substantially retains its integrity during use by a wearer when the disposable absorbent product is contacted with an oil-based solvent during such use.

In one embodiment, these goals are achieved in a disposable absorbent product comprising a topsheet, a backsheet attached to the topsheet, an absorbent structure positioned between the topsheet and the backsheet, and an elastic composite attached to the topsheet, wherein the elastic composite comprises elastic threads located between a first substrate and a second substrate wherein the first substrate is attached to the second substrate by an adhesive that exhibits the desired properties described herein.

DETAILED DESCRIPTION OF THE INVENTION

It is desired that the adhesive useful in the present invention is essentially unaffected when contacted with an oil-based solvent. As such, the adhesive substantially maintains its adhesive properties when contacted with or otherwise exposed to such an oil-based solvent.

As used herein, the term "adhesive" is used to mean that property of any material that allows the material to bond together substrates by surface attachment. Such bonding may result from the application of a pressure force, in the case of a pressure sensitive adhesive material, or a sufficiently high temperature, in the case of a hot-melt adhesive, to contact and bond the adhesive material to a substrate.

The adhesive useful in the present invention is beneficially substantially non-soluble and non-dispersible in a liquid or oil-based solvent to be contacted with a composite or disposable absorbent product comprising the adhesive. Such liquids include water, a 0.9 weight percent aqueous saline solution, synthetic urine, and body liquids such as urine, menses, and blood. Such oil-based solvents include baby oil, lotions, ointments, petroleum jellies, sunscreens, or other skin care products. Because the adhesives useful in the present invention are substantially non-soluble and non-dispersible in the liquid or solvent to be contacted with the adhesive, the adhesive properties of the adhesive will not be substantially negatively-affected when the adhesive is contacted with the liquid or solvent. This is generally in contrast to the use of an adhesive which is substantially soluble or dispersible in the liquid or solvent to be contacted with the absorbent structure since, upon contact of the liquid or solvent with the substantially soluble or dispersible adhesive, such adhesive will become substantially soluble or dispersed within the liquid or solvent so as to substantially no longer exhibit its desired adhesive properties.

As used herein, the term "substantially non-soluble" is meant to represent that substantially no soluble fraction of the adhesive can be detected in a liquid or solvent contacted with the adhesive by such known laboratory techniques as intrinsic viscosity measurements or light scattering experiments, such as those described in "Principles of Colloid and Surface Chemistry", by Paul Hiemenz (1977), incorporated herein by reference.

As used herein, the term "substantially non-dispersible" is meant to represent that, when contacted with a liquid or solvent, substantially no dispersible fraction of the adhesive material, within a size distribution range of about 1 micrometer to about 100 micrometers, can be filtered out of the liquid or solvent by using conventional filter paper.

Thus, solubility studies could, in theory, be used to identify oil-resistant adhesive polymers. In general, if an adhesive (or its components) is soluble or can be swelled by mineral oil or other oil-based solvents found in skin care products, the oil will typically plasticize and weaken the adhesive, resulting in poor bonds and render the adhesive substantially less useful. However, it has been found that oil-based solubility studies are difficult to perform and often cannot measure the effects of time and temperature on the oil-solubility. As such, solubility measurements are believed to, at best, only identify which adhesive polymers to consider for oil-resistant applications.

In contrast, it has been discovered that rheological measurements are much more important in predicting the ability of an adhesive to maintain its adhesive properties when insulted with a oil-based solvent. Rheological measurements have been found to consider the effects of time and temperature on adhesion and have been found to show the effects of oil-solubility. However, in order to form an acceptable oil-resistant bond, the viscosity of the adhesive has also been found necessary to be considered. In general, the viscosity of the adhesive should be sufficiently low at the adhesive's application temperature so as to "wet-out", or otherwise make intimate contact with, the surface of film substrates or to mechanically envelop porous nonwoven substrates. Once the adhesive makes intimate contact with the substrate, interfacial adhesion forces will typically increase the adhesive bond. The rheological properties after insult with an oil-based solvent must be sufficient to resist cohesive failure when subjected to the deformation forces of normal use, such as the walking, crawling, or other movements of a wearer or user. It has been found in the present invention that both desired rheological and viscosity properties of an adhesive must be satisfied in order for an adhesive to achieve the desired oil-resistant adhesive properties.

Rheological properties desired of the adhesive material of the present invention include exhibiting effective Elastic Modulus and Elastic Modulus in Oil values. The Elastic Modulus value of an adhesive material (G') is meant to represent the stress in phase with the strain in a sinusoidal shear deformation divided by the strain; it is a measure of the energy stored and recovered per cycle, when different systems are compared at the same strain amplitude. It is desired that the adhesive material not exhibit an Elastic Modulus value that is too low such that the adhesive lacks sufficient cohesive strength to resist delamination.

Thus, the adhesive of the present invention exhibits an Elastic Modulus value that is beneficially greater than about $4 \times 10^5$ dynes per square centimeter, suitably greater than about $6 \times 10^5$ dynes per square centimeter, more suitably greater than about $8 \times 10^5$ dynes per square centimeter, and up to about $8 \times 10^7$ dynes per square centimeter at 40° C. across the frequency range of about 0.1 to about 100 radians per second, as measured according to the methods described in the Test Procedures section herein.

The Elastic Modulus in Oil value of an adhesive material is meant to represent the coefficient of elasticity representing the ratio of stress to strain as the adhesive material is deformed under dynamic load wherein the adhesive material has been contacted with an oil-based solvent prior to its evaluation. It is desired that the adhesive material not exhibit an Elastic Modulus in Oil value that is too low such that the adhesive lacks sufficient cohesive strength to resist delamination.

Thus, the adhesive of the present invention exhibits an Elastic Modulus in Oil value that is beneficially greater than about $4 \times 10^5$ dynes per square centimeter, suitably greater than about $6 \times 10^5$ dynes per square centimeter, more suitably greater than about $8 \times 10^5$ dynes per square centimeter, and up to about $8 \times 10^7$ dynes per square centimeter at 40° C. across the frequency range of about 0.1 to about 100 radians per second, as measured according to the methods described in the Test Procedures section herein.

The adhesive of the present invention desirably exhibits an Elastic Modulus in Oil value that is beneficially at least about 50 percent, suitably at least about 75 percent, and more suitably at least about 90 percent of the Elastic Modulus value of the adhesive.

Processing properties desired of the adhesive material of the present invention include exhibiting effective Viscosity values. The Viscosity value of an adhesive material is meant to represent the apparent viscosity of the adhesive material. In general, it is desired that the adhesive material of the present invention exhibits effective Viscosity values at the temperatures of about 250° F. and about 275° F. The temperature of about 275° F. is a typical minimum temperature used in applying adhesives to a nonwoven substrate to prepare an elastic composite or a disposable absorbent product. Temperatures below about 275° F. are generally impractical to use because the adhesive will generally be too viscous to properly apply to a nonwoven substrate to result in an effective adhesive bond. Temperatures above about 375° F. are generally impractical to use because the substrate, such as a polypropylene nonwoven, onto which the adhesive is being applied may be damaged by such a high temperature.

It is thus desired that the adhesive material not exhibit a Viscosity value, at a temperature of about 275° F., that is too high such that the adhesive does not effectively penetrate a porous substrate nor effectively wet-out, or otherwise make intimate contact with, a substrate, thereby resulting in poor bonding. As such, the adhesive of the present invention exhibits a Viscosity value, at a temperature of about 275° F., that is beneficially less than about 40,000 centipoise, suitably less than about 35,000 centipoise, and more suitably less than about 30,000 centipoise, as measured according to the methods described in the Test Procedures section herein.

It is also desired that the adhesive material not exhibit a Viscosity value, at a temperature of about 250° F., that is too low such that the adhesive does not "set up" or solidify very quickly after application of the adhesive to a substrate since the adhesive may migrate or otherwise flow to undesirable locations on the substrate. Thus, the adhesive of the present invention exhibits a Viscosity value, at a temperature of about 250° F., that is beneficially greater than about 60,000 centipoise, suitably greater than about 65,000 centipoise, more suitably greater than about 70,000 centipoise, and up to about 1,000,000 centipoise, as measured according to the methods described in the Test Procedures section herein.

Adhesives useful in the present invention may be of any known type, such as a thermoplastic hot-melt adhesive, a reactive adhesive, or the like. An example of a thermoplastic hot-melt adhesive includes an adhesive material comprising a polybutylene polymer, a hydrocarbon tackifying resin, and a wax, available from Ato Findley, Inc., under the designation Findley H9220. A description of compositions of hot-melt adhesives can be found, for example, in "CRC Elastomer Technology Handbook", edited by Nicholas P. Cheremisinoff (CRC Press, 1993), Chapter 24, incorporated herein by reference.

Examples of reactive adhesives include two part polyurethanes, moisture cured polyurethanes, and epoxies. The chemistry of such reactive adhesives is known to those skilled in the art and may be found, for example, in "Contemporary Polymer Chemistry", by Harry Alcock and Frederick Lampe (Prentice Hall, 1990), incorporated herein by reference.

A more uniform dispersal of the adhesive will typically result in less of the adhesive being needed in order to achieve an effective and efficient adhesion of parts within a composite or a disposable absorbent product as compared to where the adhesive is not as uniformly dispersed. In addition, the upper and lower limits of the amount of adhesive that is to be used in a composite or a disposable absorbent product may be affected by the nature of the materials comprising the composite or disposable absorbent product. Generally speaking, one would like to use as little of the adhesive as possible.

In one aspect, the present invention concerns an elastic composite such as, for example, a containment flap, for use on a disposable absorbent product. The elastic composite has a proximal edge adapted to be joined to the disposable absorbent product and a distal edge opposite said proximal edge. The elastic composite comprises a first substrate layer, typically of a nonwoven material, a second substrate layer, typically of a nonwoven material, and an elastic member located between the first and second substrate layers, typically adjacent the distal edge of the elastic composite. In a specific embodiment of this aspect of the present invention, the elastic members are adhesively joined to the first substrate layer. In a second embodiment of this aspect of the present invention, a pattern of intermittent adhesive joins the first and second layers together and, intermittently, joins the elastic member to the first and second layers. In a third embodiment of this aspect of the present invention, the first and second layers are formed from a single, integral piece of material which is folded upon itself. A pattern of intermittent adhesive joins the first and second layers together and, intermittently, joins the elastic member to the first and second layers. Such elastic composites are described, for example, in pending U.S. patent application, Ser. No. 08/213,338, filed on Mar. 14, 1994, by David P. Kielpikowski.

In another aspect, the present invention concerns a method of making an elastic composite, such as a containment flap, for use on a disposable absorbent product. The method comprises providing a first layer of a substrate, such as a nonwoven material, traveling in a first direction. Two elastic members traveling in the first direction are attached to the first layer in a laterally-spaced relationship. A second layer of a substrate material traveling in the first direction is adhesively bonded to the first layer to form a composite having first and second longitudinal side edges. The second layer of substrate material is adhesively bonded to the first layer of substrate material such that the elastic members are located between the first and second layers and such that a first pattern of adhesive bonds is located between the elastic members. The composite is slit in the first direction between the elastic members to form two slit composites. The slit composites are then cut in a second direction perpendicular to said first direction to form a containment flap.

In another aspect, the present invention concerns a method of making an elastic composite, such as a containment flap, for use on a disposable absorbent product. The method comprises providing a single, integral piece of a substrate, such as a nonwoven material, folding said piece of substrate to provide first and second layers of substrate; positioning an elastic member between said first and second layers of substrate; and intermittently, applying an adhesive of the present invention to bond said elastic member to said first and second layers.

Specific examples of materials suitable for use as the first and second layers of substrate material include nonwoven materials, such as spunbond or meltblown thermoplastic polymers, such as polyolefins; bonded carded webs; film materials, such as polyolefin, ethylene vinyl acetate, ethyl methacrylate, and polyester films; foam materials, such as polyolefin foams; woven materials, such as woven polypropylene, polyethylene or polyester fabrics; and composites and laminates of the above nonwoven, film, foam, and woven materials. In a specific embodiment, the first and second layers of heat-fusible materials are formed from a nonwoven material such as a spunbond or meltblown polyethylene or polypropylene material. In another specific embodiment of the present invention, the first and second substrate materials are non-integrally formed. That is, the first and second layers of substrate material represent separate elements which are not joined other than by thermal, adhesive, or similar attaching techniques. Specifically, the first and second layers are not formed from an integral piece of material through a folding process. In another specific embodiment of the present invention, the first and second substrate layers are integrally formed. That is, the first and second layers are formed from a single, integral piece of material through a folding process.

The elastic member may comprise any elastomeric material capable of being elongated at least about 50 percent, alternately at least about 250 percent, alternately at least about 350 percent, and capable of recovering to a length within at least about 75 percent, more particularly, at least about 50 percent of its elongated length (original length plus elongation). The elastic member may be in the form of ribbons, individual strands, or other configurations. In one embodiment, the elastic member is in the form of individual elastomeric threads of elastomeric material. The elastic composite of the present invention may comprise a single elastic member or two or more elastic members. In one specific embodiment, the elastic member comprises a 470 decitex Lycra® thread commercially available from E. I. DuPont de Nemours and Co. Alternatively, the elastic member can be composed of a thermoplastic elastomer or a natural or synthetic rubber commercially available from J. P. S. Elastomerics Corp. The elastic member can also be composed of a heat-activatable elastic material such as Pebax®, commercially available from Atochem, Inc., which can be activated with heat treatment after the association with the containment flap.

In another aspect, the present invention concerns a disposable absorbent product having a front portion, a rear portion, and a crotch portion connecting the front and rear portions. The crotch portion has opposite longitudinal side portions. The disposable absorbent product comprises a liquid-permeable topsheet, a backsheet attached to the topsheet, and an absorbent structure positioned between the topsheet and the backsheet. A pair of elastic composite containment flaps extends longitudinally from the front portion of the disposable absorbent product to the rear portion. The containment flaps have a proximal edge and a distal edge opposite the proximal edge. The proximal edge is joined to the backsheet in the crotch portion and in the front and rear portions. The containment flaps comprise a first layer of heat-fusible material, a second layer of heat-fusible material, and an elastic member located between the first and second layers of heat-fusible material adjacent the distal edge.

Those skilled in the art will recognize materials suitable for use as the topsheet and backsheet. Examples of materials suitable for use as the topsheet are liquid-permeable materials, such as spunbonded polypropylene or polyethylene having a basis weight of from about 15 to about 25 grams per square meter. Examples of materials suitable for use as the backsheet are liquid-impervious materials, such as polyolefin films, as well as vapor-pervious materials, such as microporous polyolefin films.

A suitable absorbent structure will generally comprise a fibrous matrix into which, for example, a hydrogel-forming polymeric material is dispersed such that the fibrous matrix constrains or entraps the hydrogel-forming polymeric material.

As used herein, "hydrogel-forming polymeric material" is meant to refer to a high-absorbency material commonly referred to as a superabsorbent material. Such high-absorbency materials are generally capable of absorbing an amount of a liquid, such as synthetic urine, a 0.9 weight percent aqueous saline solution, or body liquids such as menses, urine, or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The superabsorbent material may be formed from an organic hydrogel-forming polymeric material, which may include natural materials such as agar, pectin, and guar gum, as well as synthetic hydrogel-forming polymeric materials. Synthetic hydrogel-forming polymeric materials include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines. Other suitable hydrogel-forming polymeric materials include hydrolyzed acrylonitrile grafted starch, acrylic acid grafted starch, and isobutylene maleic anhydride copolymers, and mixtures thereof. The hydrogel-forming polymeric materials are preferably lightly crosslinked to render the material substantially water insoluble yet water swellable. Crosslinking may, for example, be by irradiation or covalent, ionic, van der Waals, or hydrogen bonding. Suitable hydrogel-forming polymeric materials are typically available from various commercial vendors, such as The Dow Chemical Company, Hoechst Celanese, Allied Colloids Limited, or Stockhausen, Inc.

Suitably, the hydrogel-forming polymeric material is in the form of particles which, in the unswollen state, have maximum cross-sectional diameters within the range of from about 50 micrometers to about 1000 micrometers, and more suitably within the range of from about 100 micrometers to about 800 micrometers, as determined by sieve analysis according to American Society for Testing and Materials (ASTM) test method D-1921. It is to be understood that the particles of hydrogel-forming polymeric material falling within the size ranges described above may comprise solid particles, porous particles, or agglomerated particles comprising many smaller particles agglomerated into particles falling within the described size ranges.

The hydrogel-forming polymeric material is present in the absorbent structure of the present invention in an amount effective to result in the absorbent structure being able to absorb a desired amount of liquid under desired conditions. The hydrogel-forming polymeric material is present in the absorbent structure of the present invention in an amount beneficially from about 5 to about 95 weight percent, suitably from about 15 to about 85 weight percent, and more suitably from about 20 to about 80 weight percent, based on the total weight of the hydrogel-forming polymeric material in the absorbent structure.

As used herein, the term "fiber" or "fibrous" is meant to refer to a particulate material herein the length to diameter ratio of such particulate material is greater than about 10. Conversely, a "nonfiber" or "nonfibrous" material is meant to refer to a particulate material wherein the length to diameter ratio of such particulate material is about 10 or less.

The fibrous matrix may be formed by air-laying fibers, through a spunbond or meltblown process, a carding process, a wet-laid process, or through essentially any other means known to those skilled in the art for forming a fibrous matrix.

Methods of incorporating the hydrogel-forming polymeric material of the present invention into a fibrous matrix are known to those skilled in the art. Suitable methods include incorporating the hydrogel-forming polymeric material into the matrix during formation of the matrix, such as by air-laying the fibers of the fibrous matrix and the hydrogel-forming polymeric material at the same time or wet-laying the fibers of the fibrous matrix and the hydrogel-forming polymeric material at the same time. Alternatively, it is possible to apply the hydrogel-forming polymeric material to the fibrous matrix after formation of the fibrous matrix. Other methods include sandwiching the hydrogel-forming polymeric material between two sheets of material, at least one of which is fibrous and liquid permeable. The hydrogel-forming polymeric material may be generally uniformly located between the two sheets of material or may be located in discrete pockets formed by the two sheets. The hydrogel-forming polymeric material may be distributed in the individual layers in a generally uniform manner or may be present in the fibrous layers as a layer or other nonuniform distribution.

The fibrous matrix may be in the form of a single, integrally formed layer or of a composite comprising multiple layers. If the fibrous matrix comprises multiple layers, the layers are preferably in liquid communication with one another such that a liquid present in one fibrous layer can flow or be transported to the other fibrous layer. For example, the fibrous layers may be separated by cellulosic tissue wrap sheets known to those skilled in the art.

When the fibrous matrix comprises a single, integrally formed layer, the concentration of hydrogel-forming polymeric material may increase along the thickness of the fibrous matrix in a gradual, nonstepwise fashion or in a more stepwise fashion. Similarly, the density may decrease through the thickness in a nonstepwise manner or in a stepwise manner. The absorbent structures of the present invention may generally be of any size or dimension as long as the absorbent structure exhibits desired absorbent characteristics.

The absorbent structure of the present invention may also be used or combined with other absorbent structures, with the absorbent structure of the present invention being used as a separate layer or as an individual zone or area within a larger, composite absorbent structure. The absorbent structure of the present invention may be combined with other absorbent structures by methods well known to those skilled in the art, such as by using adhesives or simply by layering the different structures together and holding together the composite structures with, for example, tissue.

The absorbent structures according to the present invention are suited to absorb many liquids, such as water, saline, and synthetic urine, and body liquids such as urine, menses, and blood, and are suited for use in disposable absorbent products such as diapers, adult incontinent products, and bed pads; in catamenial devices such as sanitary napkins, and tampons; and in other absorbent products such as wipes, bibs, wound dressings, and surgical capes or drapes.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Test Methods
Elastic Modulus

The Elastic Modulus value of an adhesive material sample is measured for a bulk adhesive sample not suspended on any substrate. A circular adhesive material sample is prepared that has a thickness of about 2 to about 3 millimeters and has a diameter of about 25 millimeters. The adhesive material sample is placed on the lower of two 25 millimeter diameter plates of a parallel plate fixture on a Rheometrics RDS IIE Dynamic Spectrometer mechanically driven oscillatory system, available from Rheometrics, Inc., 1 Possumtown Road, N.J. 08854. The upper plate is lowered onto the adhesive material sample until the normal force meter of the system detects a slight deflection. If needed, the adhesive sample may be heated above its melting point in order to exhibit a sufficient tack so as to be adhered to the plates. The adhesive material sample is then allowed to equilibrate in a heated forced air test chamber at a temperature of about 40° C., which temperature is chosen to best simulate the body temperature of a wearer of a disposable absorbent product. A minicomputer is then used to govern the application of a 1 percent peak-to-peak shear strain to the adhesive material sample, with the frequency of the application being controlled to a fraction of a radian/second. The Elastic Modulus value for an adhesive material sample may be calculated from geometry factors, peak-to-peak amplitude of the torque signal, and the phase lag of the torque output wave. Typically, a computer using software from Rheometrics, Inc. is used to control the operation of the mechanically driven oscillatory system and to calculate the Elastic Modulus value, as well as other rheological parameters, of the adhesive material sample. The Elastic Modulus value may be displayed as a frequency sweep from about 0.1 radian per second to about 100 radians per second. The frequency range of about 0.1 radian per second to about 100 radians per second is the dynamic limit of the Rheometrics RDS IIE Dynamic Spectrometer mechanically driven oscillatory system used herein, but this frequency range also corresponds to the frequencies (or time scales) that disposable absorbent products will typically encounter in use, such as a baby walking while wearing a diaper.

Except as otherwise described herein, the Elastic Modulus value and other rheological properties are measured as outlined in the standardized test procedure ASTM D4440-93 "Standard Practice for Rheological Measurement of Polymer Melts Using Dynamic Mechanical Procedures", incorporated herein in its entirety by reference. An additional explanation of polymer rheology and measurement can be found in "Viscosity Properties of Polymers", John D. Ferry, John Wiley & Sons, Third Edition, pages 41–43, (1980), incorporated herein in its entirety by reference.

Elastic Modulus in Oil

Several circular adhesive material samples are prepared that each have a thickness of about 1 millimeter and have a diameter of about 25 millimeters. The adhesive material samples are immersed in a baby oil composition comprising mineral oil, a fragrance, and tocopheryl acetate, available from Johnson & Johnson Consumer Products, Inc., Skillman, N.J., for about 4 hours at about 40° C. A thickness of about 1 millimeter is used to better allow the baby oil to penetrate throughout the entire thickness of the adhesive material samples. The adhesive material samples are then removed from the baby oil and blotted dry with paper towels. About three of the 1 millimeter thick adhesive material samples are then stacked together to obtain a single adhesive material sample having a thickness of about 2 to about 3 millimeters. The single adhesive material sample comprising a stack of the 1 millimeter thick adhesive material samples is then placed on the lower of two 25 millimeter diameter plates of a parallel plate fixture on a Rheometrics RDS IIE Dynamic Spectrometer mechanically driven oscillatory system, and the Elastic Modulus in Oil value for an adhesive material sample is determined using essentially the same test procedure as that used to determine the Elastic Modulus value.

Viscosity

The Viscosity value of an adhesive material sample is measured for a bulk adhesive sample. A Brookfield Model DVIII RV series thermosel system viscometer, available from Brookfield Engineering Laboratories, Inc., Stoughton, Mass., is used. About 10.5 grams of an adhesive material sample is placed into a heated thermosel and allowed to heat for about 15 to 20 minutes at an initial temperature of about 400° F. (about 204° C.). A stainless steel spindle, model number SC27, is lowered into the heated thermosel and attached to the viscometer. The spindle speed is adjusted such that the displayed percent torque values are from about 20 to about 80 percent of full scale. A viscosity reading is taken about every 5 minutes until the reading has stabilized (+/−0.5 percent torque values) for about 10 minutes. The stabilized reading is recorded as the Viscosity value at that temperature. The temperature set point is then reduced about 25° F. (about 14° C.) and the process repeated.

Except as otherwise described herein, the Viscosity value is measured as outlined in the standardized test procedure ASTM D3236-88 "Standard Test Method for Apparent Viscosity of Hot Melt Adhesives and Coating Materials", incorporated herein in its entirety by reference.

EXAMPLES

Sample 1 is an adhesive material comprising a styrene-isoprene-styrene rubber block copolymer, hydrocarbon tackifying resins, and mineral oil, available from Ato Findley, Inc., 11320 Watertown Plank Road, Wauwatosa, Wis., 53226, under the designation Findley H2525A.

Sample 2 is an adhesive material comprising a polyester polymer, polar tackifying resins and polyester plasticizers, available from Ato Findley, Inc., under the designation Findley H9202.

Sample 3 is an adhesive material comprising a polyamide polymer, a rosin ester tackifying resin and a polar plasticizer, available from Ato Findley, Inc., under the designation Findley 1142-144A.

Sample 4 is an adhesive material comprising a polybutylene polymer, a hydrocarbon tackifying resin, a wax, and a nucleating agent, available from Ato Findley, Inc., under the designation Findley H9220.

Sample 5 is an adhesive material comprising a styrene-butadiene-styrene rubber block copolymer, hydrocarbon tackifying resins, and mineral oil, available from Ato Findley, Inc., under the designation Findley H4013.

Sample 6 is an adhesive material comprising a styrene-isoprene-styrene rubber block copolymer, hydrocarbon tackifying resins, and mineral oil, available from Ato Findley, Inc., under the designation Findley H2096.

Sample 7 is an adhesive material comprising a polybutylene polymer, a hydrocarbon tackifying resin, and a wax, available from Ato Findley, Inc., under the designation Findley H9214.

The samples were evaluated for Elastic Modulus and Elastic Modulus in Oil values according to the Test Methods described herein. The results of these evaluations are shown in Table 1.

The samples were also evaluated for Viscosity values according to the Test Method described herein. The results of these evaluations are shown in Table 2.

TABLE 1

Elastic Modulus and Elastic Modulus in Oil Values at 40° C. (dynes/cm$^2$)

| Adhesive Sample | 0.1 radians/sec | 1 radian/sec | 10 radians/sec | 100 radians/sec |
|---|---|---|---|---|
| *Sample 1 | $4.05 \times 10^5$ | $4.75 \times 10^5$ | $6.52 \times 10^5$ | $1.35 \times 10^6$ |
| *Sample 1 with oil | $2.41 \times 10^5$ | $2.75 \times 10^5$ | $3.41 \times 10^5$ | $5.40 \times 10^5$ |
| *Sample 2 | $2.44 \times 10^7$ | $2.49 \times 10^7$ | $2.55 \times 10^7$ | $2.62 \times 10^7$ |
| *Sample 2 with oil | $1.75 \times 10^7$ | $1.79 \times 10^7$ | $1.95 \times 10^7$ | $2.05 \times 10^7$ |
| *Sample 3 | $2.20 \times 10^7$ | $2.22 \times 10^7$ | $2.23 \times 10^7$ | $2.25 \times 10^7$ |
| *Sample 3 with oil | $2.32 \times 10^7$ | $2.36 \times 10^7$ | $2.37 \times 10^7$ | $2.39 \times 10^7$ |
| Sample 4 | $1.71 \times 10^7$ | $1.81 \times 10^7$ | $1.92 \times 10^7$ | $2.04 \times 10^7$ |
| Sample 4 with oil | $1.09 \times 10^7$ | $1.03 \times 10^7$ | $1.19 \times 10^7$ | $1.36 \times 10^7$ |
| *Sample 5 | $1.43 \times 10^5$ | $2.26 \times 10^5$ | $3.62 \times 10^5$ | $5.88 \times 10^5$ |
| *Sample 6 | $2.75 \times 10^5$ | $3.72 \times 10^5$ | $5.86 \times 10^5$ | $1.17 \times 10^6$ |
| *Sample 7 | $1.20 \times 10^7$ | $1.43 \times 10^7$ | $1.66 \times 10^7$ | $1.89 \times 10^7$ |

*Not an example of the present invention.

TABLE 2

Viscosity Values (centipoise)

| Adhesive Sample | 400° F. | 375° F. | 350° F. | 325° F. | 300° F. | 275° F. | 250° F. |
|---|---|---|---|---|---|---|---|
| *Sample 1 | 2,190 | 2,780 | 4,200 | 6,600 | 11,900 | 24,400 | 63,000 |
| *Sample 2 | 10,400 | 13,200 | 18,600 | 27,500 | 43,700 | 77,000 | 140,000 |
| *Sample 3 | 3,000 | 4,285 | 6,985 | 12,150 | 22,925 | 47,800 | >150,000 |
| Sample 4 | 3,300 | 4,300 | 6,050 | 8,830 | 13,700 | 23,400 | >150,000 |
| *Sample 7 | 4,300 | 5,480 | 7,450 | 10,500 | 17,000 | 28,000 | 46,000 |

*Not an example of the present invention.

Several of the adhesive materials were used to prepare composites comprising elastic threads and nonwoven substrates. The composites were prepared by spiral spraying about 15.5 grams of adhesive sample per square meter of substrate, at an adhesive temperature of between about 300° F. (about 150° C.) to about 365° F. (about 185° C.) and at an air temperature of about 400° F. (about 200° C.), using a 0.5 millimeter nozzle, onto a polypropylene nonwoven substrate with two polyurethane threads, available from E. I. DuPont de Nemours Company under the designation LYCRA XA polyurethane threads under about 250 percent elongation, traveling at a web speed of about 50 meters per minute and with an open time of about 0.25 seconds. After application of the adhesive, a second polypropylene nonwoven substrate layer is laminated onto the first polypropylene nonwoven substrate layer, sandwiching the polyurethane threads in between the two substrates.

Oil-insulted composites were prepared by adding about 0.2 milliliters of a baby oil composition, comprising mineral oil, a fragrance, and tocopheryl acetate, available from Johnson & Johnson Consumer Products, Inc., Skillman, N.J., directly to a one-inch inch wide bonded area of a composite and allowing the oil-insulted composite to equilibrate at room temperature (about 23° C.) for about 2 minutes.

The peel strengths of both the composites and the oil-insulted composites were determined using a T-peel test based on ASTM test method D11875-61T, incorporated herein in its entirety by reference. The test instrument used was a Sintech Model 1 tensile tester, available from MTS Corp., Minneapolis, Minn. One-inch wide (in a stretched condition) composite samples were placed in the test fixtures of the tensile tester and pulled apart at a speed of about 100 millimeters per minute. The full scale load was about 4540 grams. The results of these evaluations are shown in Table 3. The peel strength of each composite is expressed as a peak load, in grams. The energy is calculated as the area under the curve. The percent losses are calculated by dividing the oil-insulted values by the non-oil-insulted values.

TABLE 3

| Adhesive Sample | Peak Load (grams) | Peak Load Loss (%) | Energy (Kg-mm) | Energy Loss (%) |
| --- | --- | --- | --- | --- |
| *Sample 1 | 693 | — | 12.3 | — |
| *Sample 1 with oil | 196 | 72 | 3.4 | 72 |
| *Sample 2 | 110 | — | 0.9 | — |
| *Sample 2 with oil | 22 | 80 | 0.1 | 89 |
| *Sample 3 | 181 | — | 1.8 | — |
| *Sample 3 with oil | 63 | 65 | 0.5 | 72 |
| Sample 4 | 767 | — | 11.2 | — |
| Sample 4 with oil | 491 | 36 | 5.9 | 47 |

*Not an example of the present invention.

From this data, it is apparent that Sample 4 retains its peel strength after an oil-insult better than the other samples. A minimum peak peel strength level of about 300 grams is generally desirable since this is the force typically required for destruction of a typical nonwoven polypropylene substrate. Below such a minimum peak peel strength level, the adhesive bonds can potentially fail, allowing exposure of the elastic threads or other product components.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastic composite comprising an elastic member located between a first substrate and a second substrate wherein the first substrate is attached to the second substrate by an adhesive that exhibits the following properties:

a) an Elastic Modulus value that is greater than about $4 \times 10^5$ dynes per square centimeter at 40° C. across the frequency range of about 0.1 to about 100 radians per second;
   b) an Elastic Modulus in Oil value that is greater than about $4 \times 10^5$ dynes per square centimeter at 40° C. across the frequency range of about 0.1 to about 100 radians per second;
   c) a Viscosity value of less than about 40,000 centipoise at a temperature of about 275° F.; and
   d) a Viscosity value of greater than about 60,000 centipoise at a temperature of about 250° F., wherein the elastic member is not an adhesive.

2. The elastic composite of claim 1 wherein the adhesive exhibits an Elastic Modulus value that is greater than about $6 \times 10^5$ dynes per square centimeter at 40° C. across the frequency range of about 0.1 to about 100 radians per second.

3. The elastic composite of claim 1 wherein the adhesive exhibits an Elastic Modulus in Oil value that is greater than about $6 \times 10^5$ dynes per square centimeter at 40° C. across the frequency range of about 0.1 to about 100 radians per second.

4. The elastic composite of claim 1 wherein the adhesive exhibits a Viscosity value of less than about 35,000 centipoise at a temperature of about 275° F.

5. The elastic composite of claim 1 wherein the adhesive exhibits a Viscosity value of greater than about 65,000 centipoise at a temperature of about 250° F.

6. The elastic composite of claim 1 wherein the adhesive exhibits an Elastic Modulus value that is greater than about $6 \times 10^5$ dynes per square centimeter at 40° C. across the frequency range of about 0.1 to about 100 radians per second, an Elastic Modulus in Oil value that is greater than about $6 \times 10^5$ dynes per square centimeter at 40° C. across the frequency range of about 0.1 to about 100 radians per second, a Viscosity value of less than about 35,000 centipoise at a temperature of about 275° F., and a Viscosity value of greater than about 65,000 centipoise at a temperature of about 250° F.

7. The elastic composite of claim 6 wherein the adhesive exhibits an Elastic Modulus value that is greater than about $8 \times 10^5$ dynes per square centimeter at 40° C. across the frequency range of about 0.1 to about 100 radians per second, an Elastic Modulus in Oil value that is greater than about $8 \times 10^5$ dynes per square centimeter at 40° C. across the frequency range of about 0.1 to about 100 radians per second, a Viscosity value of less than about 30,000 centipoise at a temperature of about 275° F., and a Viscosity value of greater than about 70,000 centipoise at a temperature of about 250° F.

8. The elastic composite of claim 1 wherein the adhesive comprises a polybutylene polymer.

9. The elastic composite of claim 8 wherein the adhesive further comprises a tackifying resin, a wax, and a nucleating agent.

10. The elastic composite of claim 1 wherein the first substrate is selected from the group consisting of nonwoven materials, bonded carded webs, film materials, foam materials, and woven materials and the second substrate is selected from the group consisting of nonwoven materials, bonded carded webs, film materials, foam materials, and woven materials.

11. The elastic composite of claim 1 wherein the first substrate is a nonwoven material and the second substrate is a nonwoven material.

12. The elastic composite of claim 1 wherein the first substrate is a nonwoven material prepared from a polyolefin and the second substrate is a nonwoven material prepared from a polyolefin.

13. The elastic composite of claim 1 wherein the elastic member is capable of being elongated at least about 50 percent of the original length of the elastic member.

14. A method of preparing an elastic composite, the method comprising providing a first substrate, locating an elastic member onto the first substrate, and then bonding a second substrate to the first substrate with an adhesive, wherein the elastic member is positioned between the first substrate and the second substrate, and wherein the adhesive exhibits the following properties:

a) an Elastic Modulus value that is greater than about $4 \times 10^5$ dynes per square centimeter at 40° C. across the frequency range of about 0.1 to about 100 radians per second;

b) an Elastic Modulus in Oil value that is greater than about $4 \times 10^5$ dynes per square centimeter at 40° C. across the frequency range of about 0.1 to about 100 radians per second;

c) a Viscosity value of less than about 40,000 centipoise at a temperature of about 275° F.; and d) a Viscosity value of greater than about 60,000 centipoise at a temperature of about 250° F., wherein the elastic member is not an adhesive.

15. The method of claim 14 wherein the adhesive exhibits an Elastic Modulus value that is greater than about $8 \times 10^5$ dynes per square centimeter at 40° C. across the frequency range of about 0.1 to about 100 radians per second, an Elastic Modulus in Oil value that is greater than about $8 \times 10^5$ dynes per square centimeter at 40° C. across the frequency range of about 0.1 to about 100 radians per second, a Viscosity value of less than about 30,000 centipoise at a temperature of about 275° F., and a Viscosity value of greater than about 70,000 centipoise at a temperature of about 250° F.

16. The method of claim 14 wherein the adhesive comprises a polybutylene polymer.

17. The method of claim 15 wherein the adhesive further comprises a tackifying resin, a wax, and a nucleating agent.

18. The method of claim 14 wherein the first substrate is selected from the group consisting of nonwoven materials, bonded carded webs, film materials, foam materials, and woven materials and the second substrate is selected from the group consisting of nonwoven materials, bonded carded webs, film materials, foam materials, and woven materials.

* * * * *